(12) United States Patent
Choi et al.

(10) Patent No.: US 10,308,655 B2
(45) Date of Patent: Jun. 4, 2019

(54) METHOD OF TREATING CROHN'S DISEASE COMPRISING A TLR2 ANTAGONIST

(71) Applicant: AJOU UNIVERSITY INDUSTRY-ACADEMIC COOPERATION FOUNDATION, Suwon-si, Gyeonggi-do (KR)

(72) Inventors: Sang Dun Choi, Suwon-si (KR); Prasannavenkatesh Durai, Suwon-si (KR); Asma Achek, Suwon-si (KR)

(73) Assignee: AJOU University Industry-Academic Cooperation Foundation, Suwon-si, Gyeonggi-do (KR)

( * ) Notice: Subject to any disclaimer, the term of this patent is extended or adjusted under 35 U.S.C. 154(b) by 0 days.

(21) Appl. No.: 15/578,086

(22) PCT Filed: Dec. 23, 2015

(86) PCT No.: PCT/KR2015/014202
§ 371 (c)(1),
(2) Date: Nov. 29, 2017

(87) PCT Pub. No.: WO2016/195194
PCT Pub. Date: Dec. 8, 2016

(65) Prior Publication Data
US 2018/0148455 A1    May 31, 2018

(30) Foreign Application Priority Data
May 29, 2015  (KR) .................. 10-2015-0076217
Dec. 9, 2015   (KR) .................. 10-2015-0175045

(51) Int. Cl.
| | | |
|---|---|---|
| *C07D 487/04* | (2006.01) | |
| *A61P 1/00* | (2006.01) | |
| *A61P 27/02* | (2006.01) | |
| *A61P 1/02* | (2006.01) | |
| *A61P 7/00* | (2006.01) | |
| *A61P 19/06* | (2006.01) | |
| *A61P 25/28* | (2006.01) | |
| *A61P 11/06* | (2006.01) | |
| *A61P 31/12* | (2006.01) | |
| *A61P 17/00* | (2006.01) | |
| *A61P 19/02* | (2006.01) | |
| *A61P 37/08* | (2006.01) | |
| *A61P 13/12* | (2006.01) | |

(Continued)

(52) U.S. Cl.
CPC .......... *C07D 487/04* (2013.01); *A61K 9/0053* (2013.01); *A61K 31/4178* (2013.01); *A61K 31/4453* (2013.01); *A61K 31/496* (2013.01); *A61K 31/506* (2013.01); *A61K 31/5377* (2013.01); *A61K 31/551* (2013.01); *A61P 1/00* (2018.01); *A61P 1/02* (2018.01); *A61P 1/04* (2018.01); *A61P 7/00* (2018.01); *A61P 11/00* (2018.01); *A61P 11/06* (2018.01); *A61P 13/12* (2018.01); *A61P 17/00* (2018.01); *A61P 19/02* (2018.01); *A61P 19/06* (2018.01); *A61P 25/28* (2018.01); *A61P 27/00* (2018.01); *A61P 27/02* (2018.01); *A61P 27/16* (2018.01); *A61P 29/00* (2018.01); *A61P 31/12* (2018.01); *A61P 37/08* (2018.01); *C07C 251/24* (2013.01); *C07D 207/277* (2013.01); *C07D 211/26* (2013.01); *C07D 211/34* (2013.01); *C07D 243/08* (2013.01); *C07D 265/30* (2013.01); *C07D 333/78* (2013.01); *C07D 401/06* (2013.01); *C07D 401/12* (2013.01); *C07D 401/14* (2013.01); *C07D 403/06* (2013.01); *C07D 403/12* (2013.01); *C07D 409/12* (2013.01); *C07D 471/04* (2013.01); *C07D 471/10* (2013.01)

(58) Field of Classification Search
CPC .............................. C07D 487/04; A61P 27/02
See application file for complete search history.

(56) References Cited

U.S. PATENT DOCUMENTS

| | | | |
|---|---|---|---|
| 7,550,501 B2 * | 6/2009 | Chow ..................... | C07F 9/091 514/419 |
| 2007/0167409 A1 | 7/2007 | Chow et al. | |
| 2011/0105426 A1 | 5/2011 | Pearlman | |

FOREIGN PATENT DOCUMENTS

| | | |
|---|---|---|
| KR | 10-2011-0071108 A | 6/2011 |
| KR | 10-2011-0081336 A | 7/2011 |
| WO | 2009/019260 A2 | 2/2009 |

OTHER PUBLICATIONS

Compound of CAS RN 1147401-24-8, May 19, 2009.*

(Continued)

*Primary Examiner* — Yong L Chu
(74) *Attorney, Agent, or Firm* — Vorys, Sater, Seymour and Pease LLP; Mih Suhn Koh

(57) ABSTRACT

The present disclosure relates to a novel small molecule TLR2 antagonist, and particularly, to 19 novel TLR2 antagonists, a pharmaceutical composition, including the antagonists, for preventing or treating inflammatory diseases, and a TLR4 regulator.
The novel TLR2 antagonists according to the present disclosure can be effectively used as a preparation for oral administration by having low molecular weight and high oral bioavailability, and can be useful in pharmaceutical compositions for preventing or treating inflammatory diseases since the secretion of IL-8 is effectively inhibited and in vivo cytotoxicity is not induced. In addition, the novel TLR2 antagonists according to the present disclosure can be used as a TLR4 regulator.

2 Claims, 20 Drawing Sheets
(1 of 20 Drawing Sheet(s) Filed in Color)

(51) Int. Cl.

| | | |
|---|---|---|
| *A61P 27/16* | (2006.01) | |
| *A61P 11/00* | (2006.01) | |
| *A61P 29/00* | (2006.01) | |
| *A61P 1/04* | (2006.01) | |
| *A61P 27/00* | (2006.01) | |
| *C07C 251/24* | (2006.01) | |
| *C07D 207/277* | (2006.01) | |
| *C07D 211/26* | (2006.01) | |
| *C07D 211/34* | (2006.01) | |
| *C07D 243/08* | (2006.01) | |
| *C07D 265/30* | (2006.01) | |
| *C07D 333/78* | (2006.01) | |
| *C07D 401/06* | (2006.01) | |
| *C07D 401/12* | (2006.01) | |
| *C07D 401/14* | (2006.01) | |
| *C07D 403/06* | (2006.01) | |
| *C07D 403/12* | (2006.01) | |
| *C07D 409/12* | (2006.01) | |
| *C07D 471/04* | (2006.01) | |
| *C07D 471/10* | (2006.01) | |
| *A61K 9/00* | (2006.01) | |
| *A61K 31/5377* | (2006.01) | |
| *A61K 31/551* | (2006.01) | |
| *A61K 31/4178* | (2006.01) | |
| *A61K 31/4453* | (2006.01) | |
| *A61K 31/496* | (2006.01) | |
| *A61K 31/506* | (2006.01) | |

(56) References Cited

OTHER PUBLICATIONS

Compound of CAS RN 1252365-64-2, Nov. 10, 2010.*
Honig et al. Journal of Translational Medicine 2004, 2(44), p. 1-8 (Year: 2004).*
Schafer et al. Drug Discovery Today, 2008, 13 (21/22), 913-916 (Year: 2008).*
"Crohn's disease" in Wikipedia, downloaded 2018.*
International Search Report of International Application No. PCT/KR2015/014202, "Novel TLR2 Antagonists", 3 pgs., dated Nov. 30, 2016.
Written Opinion of International Application No. PCT/KR2015/014202, "Novel TLR2 Antagonists", 6 pgs., dated Nov. 30, 2016.
Yamada (ed.), Textbook of Gastroenterology 5th edition, p. 157 of "Chapter 7, The mucosal immune system and gastrointestinal inflammation", Cominelli et al., pp. 133-168, (2011).
Daig et al., "Increased interleukin 8 expression in the colon mucosa of patients with inflammatory bowel disease", Gut, vol. 38, No. 2, pp. 216-222, (1996).
Izutani et al., "Increased Expression of Interleukin-8 mRNA in Ulcerative Colitis and Crohn's Disease Mucosa and Epithelial Cells", Inflammatory Bowel Diseases, vol. 1, No. 1, pp. 37-47, (1995).
Liu et al., "Sparstolonin B Attenuates Hypoxia-Induced Apoptosis, Necrosis and Inflammation in Cultured Rat Left Ventricular Tissue Slices", Cardiovasc Drugs Ther (2014) 28(5): 433-439.
Shirey et al., "The TLR4 antagonist Eritoran protects mice from lethal influenza infection", Nature, (2013) 497(7450): 498-502.

* cited by examiner

FIG.2

Central domain
LRR9
| hTLR2 | TNSLIKKFTFRNVKITDESLFQVKLLN | 274 |

| hTLR1 | TNPKLSSLTLNNIETTNSIRIQLV | 268 |

LRR10
| hTLR2 | QISGLLELEFDDCTLNGVGFRASDNDRVI | 304 |

| hTLR1 | WHTTVWYSSISNVKQGQLDFRDFDY | 294 |

LRR11
| hTLR2 | DPGKVETLTIRRLHIPRFYLFYDLSTLYS | 333 |

| hTLR1 | SGTSLKALSHQVSDVFPQSYE | 323 |

C-terminal domain
LRR12
| hTLR2 | LTERKRITVENVFLVPCLLSQ | 357 |

| hTLR1 | SNMNIKNFTSGVHMLCPS | 345 |

LRR13
| hTLR2 | HLKSLEYLDLSENLMVEELKNSACED | 384 |

☐ $Pam_3CSK_4$ binding and destabilizing

▨ $Pam_3CSK_4$ binding but neutral

▨ No $Pam_3CSK_4$ binding but destabilizing

▨ Neither $Pam_3CSK_4$ binding nor destabilizing

FIG.12
S06690562
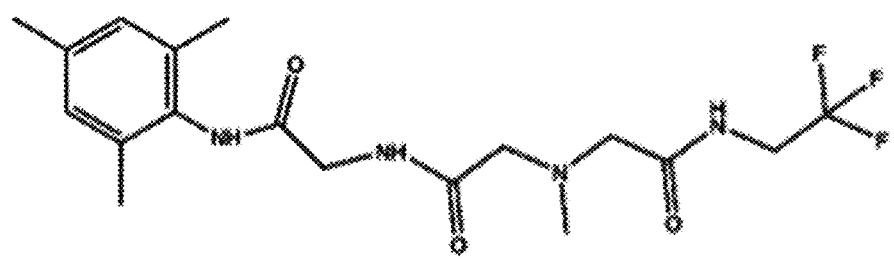
S01688300
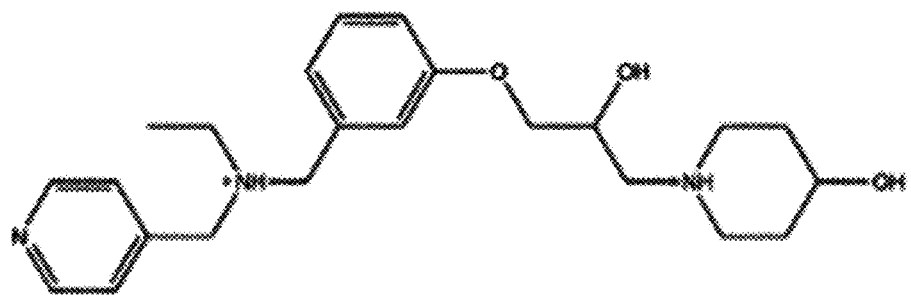
S01382085
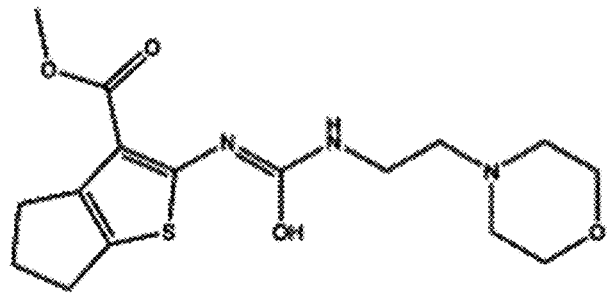

METHOD OF TREATING CROHN'S DISEASE COMPRISING A TLR2 ANTAGONIST

TECHNICAL FIELD

The present disclosure relates to a novel small molecule TLR2 antagonist, and particularly, to 19 novel TLR2 antagonists, a pharmaceutical composition, including the antagonists, for preventing or treating inflammatory diseases, and a TLR4 regulator.

BACKGROUND ART

Virtual screening is an in silico approach method capable of rapidly anticipating the binding of a molecule from a compound library to a target receptor and effectively prioritizing molecules with related biological activities for further validation experiments. In order to overcome a high cost problem of the disadvantage of an experimental high-throughput screening (HTS) method, a large amount of compound library requires selective downsizing into a small set that can include a specific target drug. To this end, virtual screening has been increasingly applied in drug discovery projects prior to the experimental HTS. The application of various virtual screening techniques can significantly increase the efficiency of research in the field of drug discovery. One of the widely applied techniques in virtual screening is to compare two-dimensional (2D) properties between the experimentally determined ligands and the molecules of a compound library. In this approach method, the structural characteristics of molecules are expressed by the kind of constituent atoms and their bond levels. Another technique is to use the three-dimensional structural properties of molecules to compare similarities between molecules. Three-dimensional structure-based virtual screening approach methods are classified mainly into an approach method based on ligand coordinates and an approach method based on receptor coordinates. Like a two-dimensional (2D) method, the ligand-based approach method searches for molecules similar to the experimentally determined active ligand by comparing the three-dimensional structure properties between the molecules. This approach method is typically applied where only limited information about a target receptor is available. The ligand-based method essentially includes a comparative analysis process of structural properties, and accordingly, the application thereof necessarily requires information acquisition of the known active ligand. One of the available programs, Rapid Overlay of Chemical Structures (ROCS), uses an overlapping method for large form-based comparisons. ROCS adopts a method of comparing the structural similarities between two molecules based on the three-dimensional form. The three-dimensional form of the parameterized specifically expressed molecule uses Gaussian-based overlap to obtain the optimal alignment of the largest volume overlapping between two molecules. Since the similarity of chemical properties as well as the morphological similarity of molecules is a crucial factor in biological activity, the overlap between the functional groups that a compound has is additionally calculated using a color force field. The conformational flexibility of molecules can be considered by precomputing conformers ensembles in advance and sequentially comparing each of them. The excellence of the ROCS method has been reported through a number of research literature. When high-resolution coordinates of a target receptor are available, molecular docking is a common method of selection in virtual screening. Docking is used to quantify the binding affinity between molecules and receptors from a compound library by computer operation and to predict the binding potential between them. In essence, this method does not necessarily require information about a compound that is active for a drug target, but it can increase performance by incorporating the binding properties of a known active material into a docking process.

An antagonist, on the other hand, is a substance that binds to a receptor of a certain agonist but does not exhibit the physiological action through the receptor. TLR2 (Toll-like receptor 2) is present in the plasma membrane or endosome and belongs to the first line of defense of host defense in the inflammatory response. Signaling associated with TLR2 has been reported to have an association with cancer, tuberculosis, anemia, atopic dermatitis, and atherosclerosis. In particular, antagonists of TLR2 have become a major pharmacological target due to its inhibitory effect on inflammatory diseases. Accordingly, there is a need to screen for antagonists of novel TRL2 that can be used pharmacologically. In particular, research for screening antagonists that are small molecules is needed.

DISCLOSURE

Technical Problem

As a result of screening using a computer on the basis of a pharmacophore model targeted on about 7 million compounds, the present inventors selected a novel small molecule TLR2 antagonist which can be used for the prevention or treatment of inflammatory diseases, and completed the present disclosure.

It is an object of the present disclosure to provide a novel TLR2 antagonist.

Another object of the present disclosure is to provide a pharmaceutical composition for the prevention or treatment of an inflammatory disease including the TLR2 antagonists, an oral administration agent, and a TLR4 regulator including the antagonists.

Advantageous Effects

Since the novel TLR2 antagonist according to the present disclosure has a low molecular weight and a high oral bioavailability, it can be effectively used as an oral administration agent, effectively inhibits IL-8 secretion and does not cause toxicity in vivo, and thus can be usefully used as a pharmaceutical composition for preventing or treating inflammatory diseases. The novel TLR2 antagonists according to the invention can also be used as regulators of TLR4.

DESCRIPTION OF DRAWINGS

The patent or application file contains at least one drawing executed in color. Copies of this patent or patent application publication with color drawing(s) will be provided by the Office upon request and payment of the necessary fee.

FIG. 2 is a diagram illustrating the results of confirming the major residues that affect binding based on the calculated free energy as a result of In Silico Alanine Scanning Mutagenesis.

FIG. 12 is a diagram illustrating the two-dimensional structure of three screened compounds (S06690562, S01688300, S01382085).

MODES OF THE INVENTION

Figure 1:
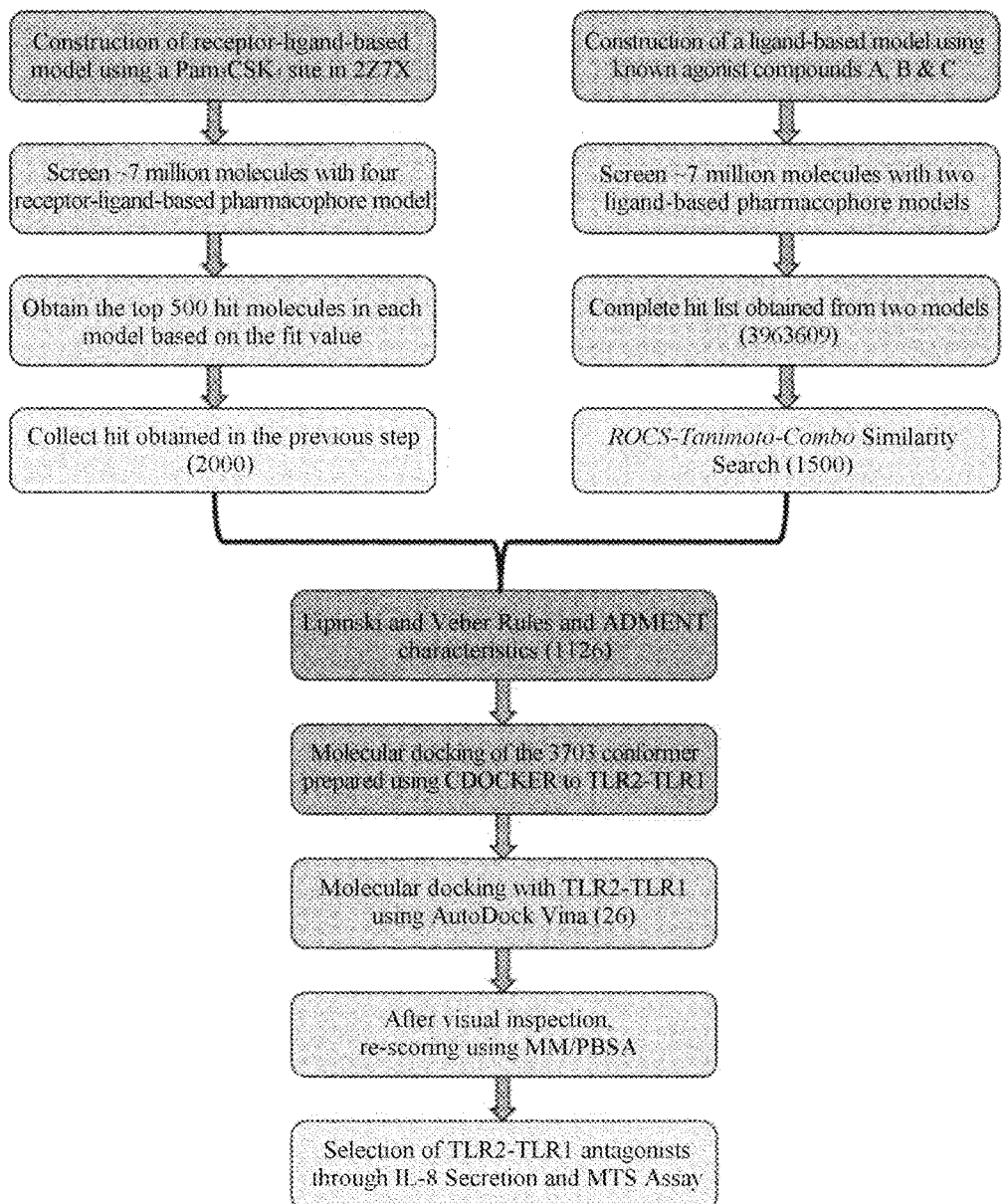
FIG. 1 is a diagram briefly illustrating the overall steps for identifying TLR2 antagonists.

Hereinafter, the present disclosure will be described in detail.

The present disclosure provides at least one TLR2 (Toll-like receptor 2) antagonist selected from the group consisting of the compounds illustrated in Table 1 below.

TABLE 1

| Compound names | Compound structures |
| --- | --- |
| S02546436 | 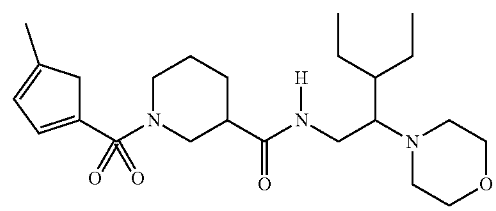 |
| S02276077 | 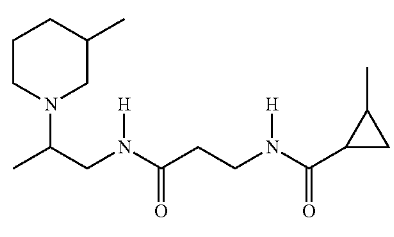 [SMILES: CC1CCCN(C(C)CNC(=O)CCNC(=O)C2CC2C)C1] |
| S06696686 | 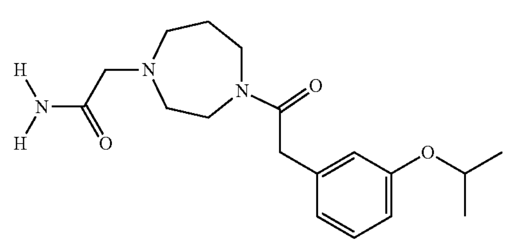 [SMILES: CC(C)Oc1cccc(CC(=O)N2CCCN(CC(N)=O)CC2)c1] |

TABLE 1-continued

| Compound names | Compound structures |
|---|---|
| S06690562 | 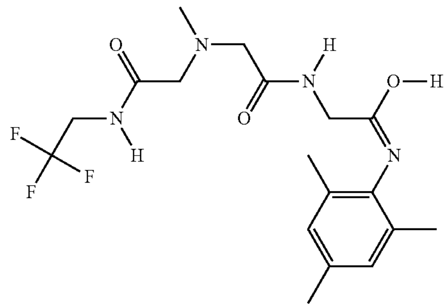 [SMILES: Cc1cc(C)c(/N=C(/O)CNC(=O)CN(C)CC(=O)NCC(F)(F)F)c(C)c1] |
| S06713271 | 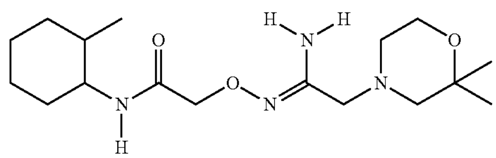 [SMILES: CC1CCCCC1NC(=O)CO/N=C(\N)CN1CCOC(C)(C)C1] |
| S02396152 | 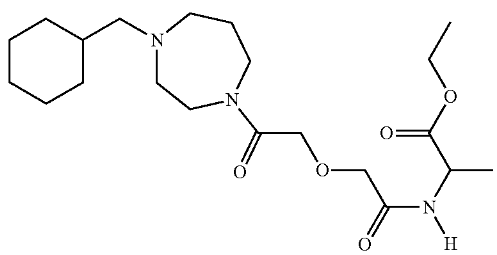 [SMILES: CCOC(=O)C(C)NC(=O)COCC(=O)N1CCCN(CC2CCCCC2)CC1] |
| S01525559 | 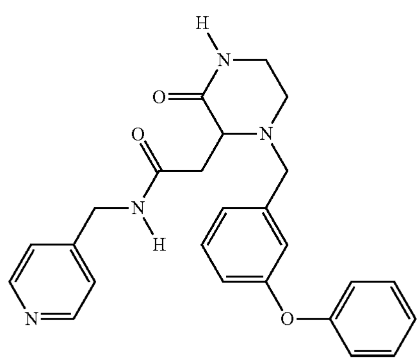 [SMILES: O=C(CC1C(=O)NCCN1Cc1cccc(Oc2ccccc2)c1)NCc1ccncc1] |
| S06542401 | 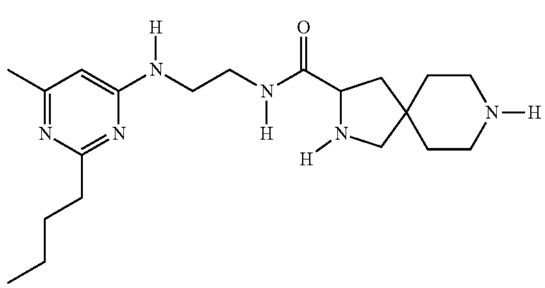 [SMILES: CCCCc1nc(C)cc(NCCNC(=O)C2CC3(CCNCC3)CN2)n1] |

TABLE 1-continued
| Compound names | Compound structures |
|---|---|
| S01739292 | 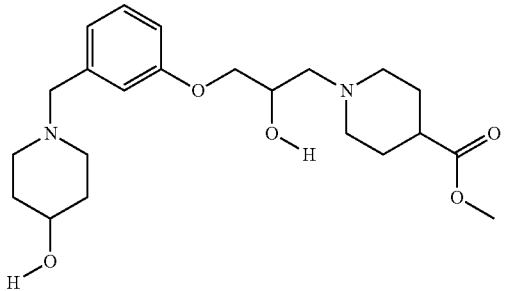 [SMILES: COC(=O)C1CCN(CC(O)COc2cccc(CN3CCC(O)CC3)c2)CC1] |
| S01688300 | 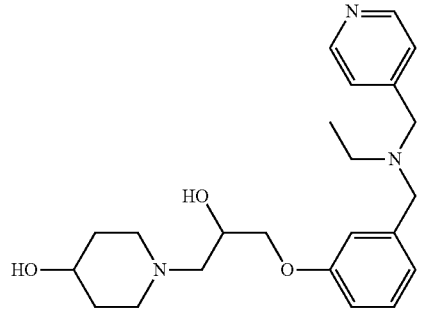 [SMILES: CCN(Cc1ccncc1)Cc1cccc(OCC(O)CN2CCC(O)CC2)c1] |
| S06570841 | 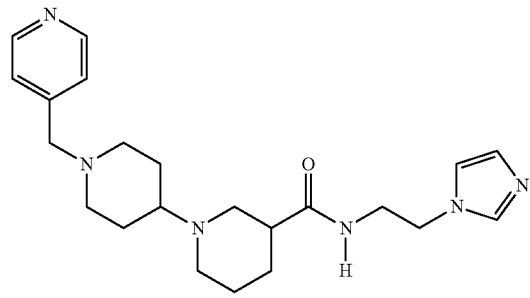 [SMILES: O=C(NCCn1ccnc1)C1CCCN(C2CCN(Cc3ccncc3)CC2)C1] |
| S06570001 | 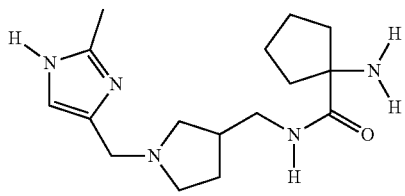 [SMILES: Cc1nc(CN2CCC(CNC(=O)C3(N)CCCC3)C2)c[nH]1] |
| S06568641 | 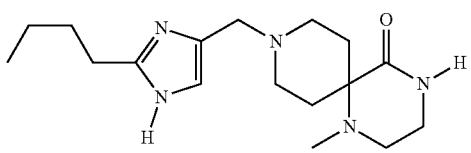 [SMILES: CCCCc1nc(CN2CCC3(CC2)C(=O)NCCN3C)c[nH]1] |

TABLE 1-continued

| Compound names | Compound structures |
| --- | --- |
| S06572801 | 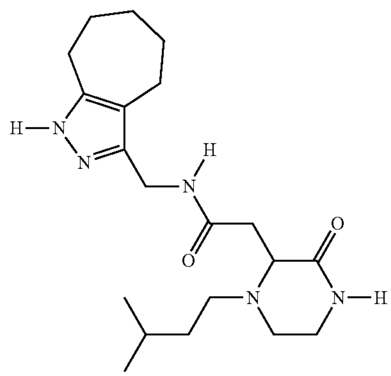 [SMILES: CC(C)CCN1CCNC(=O)C1CC(=O)NCc1n[nH]c2c1CCCCC2] |
| S01577528 | 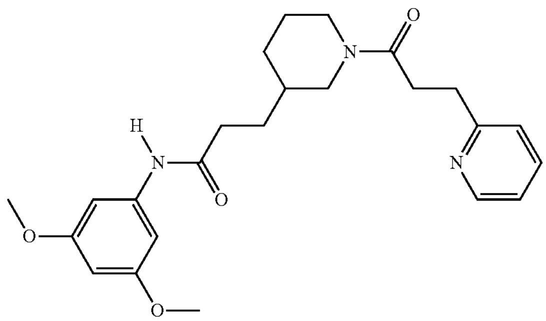 [SMILES: COc1cc(NC(=O)CCC2CCCN(C(=O)CCc3ccccn3)C2)cc(OC)c1] |
| S01382085 | 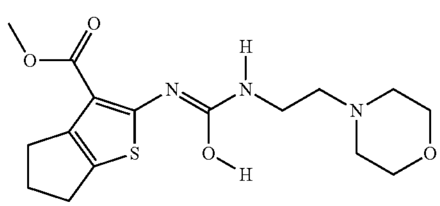 [SMILES: COC(=O)c1c(/N=C(\O)NCCN2CCOCC2)sc2c1CCC2] |
| S01442577 | 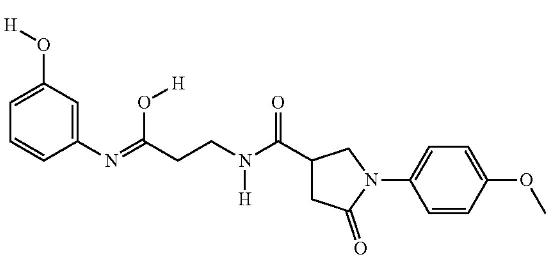 [SMILES: COc1ccc(N2CC(C(=O)NCC/C(O)=N/c3cccc(O)c3)CC2=O)cc1] |
| S01414289 | 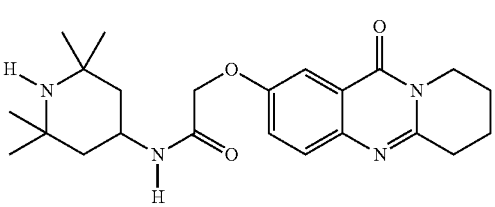 [SMILES: CC1(C)CC(NC(=O)COc2ccc3nc4n(c(=O)c3c2)CCCC4)CC(C)(C)N1] |

TABLE 1-continued

| Compound names | Compound structures |
|---|---|
| S01292238 | (structure shown) |

The "TLR2 (Toll-like receptor 2)" of the present disclosure means a substance which is located on the cell surface of monocytes, macrophages, neutrophils, and the like, and functions as receptors for bacterial components (lipid polysaccharides, peptide glycans, adipocyte proteins, mycobacterial glycolipids, and heat shock proteins (hsp)). When TLR2 is stimulated, the cells are activated to stimulate the production of inflammatory cytokines and inflammatory mediators (TNF, IL-1, IL-6, IL-8, NO, etc.).

In the present disclosure, the term "antagonist" means a substance which binds to a receptor of a drug or some agonist which serves to attenuate some or all of its action by the combination of a drug with another drug, but does not exhibit physiological action through its receptor. Accordingly, the TLR2 antagonist has a strong binding ability to TLR2, so that it can partially inhibit TLR2-related signaling at the micro-molecular level but not completely abolish it.

The "TLR2 antagonist" of the present disclosure includes 19 compounds of Table 1 and preferably 6 compounds (S02546436, S02276077, S06696686, S06690562, S01688300, S01382085), more preferably three compounds (S06690562, S01688300, S01382085). The TLR2 antagonists of the present disclosure may also include, without limitation, the 19 compounds of Table 1 as well as analogs thereof having the same, similar activity.

Some of the compounds, such as S06690562, are tautomeric molecules and may exist in the enol or keto form by tautomerization according to pH.

The TLR2 antagonist of the present disclosure is characterized by being a small molecule because it has no fatty acyl residues. Since such molecular weight reduction is advantageous in pharmacokinetics, the antagonists and their analogs of the present disclosure can be usefully used to design drugs as an active ingredient of pharmaceutical compositions.

The "small molecule" means an organic compound having a molecular weight of preferably 900 Da or less, but not limited thereto.

The TLR2 antagonists of the present disclosure have a different core structure from those previously presented as antagonists of TLR2. In addition, the 19 compounds illustrated in Table 1 have each different structure.

The 19 TLR2 antagonists of the present disclosure include all substances that are purchased and used or synthesized by methods known in the pertinent field.

In addition, the present disclosure also provides a pharmaceutical composition for the prevention or treatment of inflammatory diseases including the TLR2 (Toll-like receptor 2) antagonist.

The term "inflammatory disease" as used herein includes, but not limited to, edema, dermatitis, allergies, atopy, asthma, conjunctivitis, periodontitis, rhinitis, otitis, sore throat, tonsillitis, pneumonia, gastric ulcer, gastritis, Crohn's disease, colitis, hemorrhoids, gout, ankylosing spondylitis, rheumatic fever, lupus, fibrornyalgia, psoriatic arthritis, osteoarthritis, rheumatoid arthritis, periarthritis of shoulder, tendinitis, peritenonitis, myosins, hepatitis, cystitis, nephritis, sjogren's syndrome, and multiple sclerosis.

As used herein, the term "prevention" means any action that inhibits or slows the progression of an inflammatory disease upon administration of the composition of the present disclosure.

As used herein, the term "treatment" means any action which improves or beneficially changes an inflammatory disease by administration of a composition of the present disclosure.

The compositions of the present disclosure include a pharmaceutically acceptable carrier. The carrier which is included and allowed in the pharmaceutical composition of the present disclosure is usually used in the preparation, and includes lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, mineral oil, saline solution, PBS (phosphate buffered saline), or a medium, etc., but is not limited thereto.

The pharmaceutical composition of the present disclosure may further include a lubricant, a wetting agent, a sweetening agent, a flavoring agent, an emulsifying agent, a suspending agent, a preservative, etc. in addition to the above components. Suitable pharmaceutically acceptable carriers and preparations are described in detail in Remington's Pharmaceutical Sciences (19th ed., 1995).

The pharmaceutical composition of the present disclosure can also be used together, simultaneously, and sequentially, including additional components that can be used to prevent or treat inflammatory diseases associated with TLR2.

The appropriate dosage of the pharmaceutical composition of the present disclosure may be prescribed in various ways depending on factors such as the preparation method, administration method, age, body weight, sex, pathological condition, food, administration time, route of administration, excretion speed and response susceptibility of a patient.

In addition, the present disclosure provides an oral administration agent for the prevention or treatment of inflammatory diseases including the TLR2 (Toll-like receptor 2) antagonist.

Since the TLR2 antagonist of the present disclosure is characterized by being a small molecule, it has a good oral bioavailability. In the present disclosure, the bioavailability refers to a fraction of the amount of drug administered that falls within the subcategories of absorption of the drug and reaches the systemic circulation. Accordingly, when the oral administration agent for the prevention or treatment of inflammatory diseases including the TLR2 antagonist of the present disclosure is orally administered, there is an effect in that the drug reaches the systemic circulation at a high rate.

Oral administration agents according to the present disclosure may be administered as a formulation selected from solid pharmaceutical preparations such as tablets, pills, capsules, powders and granules, or pharmaceutically acceptable aqueous solutions, suspensions and emulsions, syrups, pharmaceutical preparations dissolved in use and elixir oral liquid pharmaceutical preparations.

In addition, the present disclosure provides a method for screening a TLR2 (toll-like receptor 2) antagonist, including: (a) constructing a receptor-ligand-based pharmacophore model; (b) constructing a ligand-based pharmacophore model; (c) screening the results of (a) and (b); and (d) performing a biological experiment with the result of (c) for screening.

The term "pharmacophore" in the present disclosure means a characteristic of a molecule required for molecular recognition of a ligand. The "pharmacophore model" describes how various ligands can bind to a common receptor site and can be used for the virtual screening of novel ligands that bind to the same receptor.

In the present disclosure, a method for constructing "receptor-ligand-based pharmacophore models" includes a technique of inducing In Silico Alanine Scanning Mutagenesis including a process in which the residues of the binding site between $Pam_3CSK_4$ and TLR2-TLR1 in the TLR2-TLR1-$Pam_3CSK_4$ complex are mutated to alanine and a technique of targeting the binding site of TLR2-TLR1-$Pam_3CSK_4$ by using a Receptor-ligand Pharmacophore Generation protocol to confirm the major residues that play an important role in binding. If a technique of using a computer is used, there is an effect of time saving and cost saving.

The "$Pam_3CSK_4$" of the present disclosure is an agonist of TLR2 and TLR1

The method for constructing a "ligand-based Pharmacophore model" in the present disclosure includes identifying the characteristics of a pharmacophore model using an antagonist of a known small molecule TLR2.

The screening the identified results from the pharmacophore model constructed in the present disclosure includes screening a fit value, molecular similarity, drug-like compounds, molecular docking and scoring, and rescoring docking complex. Through the screening process, a candidate compound of an antagonist of TLR2, which is a small molecule having drug similarity due to its excellent binding ability to TLR2, can be obtained.

The "biological experiments" in the present disclosure include analysis of IL-8 secretion, cell viability. It can be confirmed whether the candidate compound of the TLR2 antagonist selected through the biological experiments serves as a TLR2 antagonist, and whether toxicity is shown.

In addition, the present disclosure provides at least one TLR4 (Toll-like receptor 4) regulator selected from the group consisting of the compounds of Table 1 above.

As used herein, the term "regulator" refers to a substance that increases or decreases levels of a molecule to a measurable extent, including, but not limited to, inhibitors, antagonists, effectors, and the like.

The TLR4 of the present disclosure is characterized by having structural and functional similarity with TLR2, and a compound screened with an antagonist of TLR2 may have regulator activity of TLR4. Accordingly, 19 compounds of the present disclosure, TLR2 antagonists, can be utilized as regulators of TLR4.

Terms not otherwise defined herein have meanings as commonly used in the art to which the present disclosure pertains.

Hereinafter, the present disclosure will be described in more detail with reference to examples. However, these examples are for illustrative purposes only, and the scope of the present disclosure is not limited to these examples.

Statistical analysis shown in the following examples was performed by defining, as statistical significance level, P value (less than or equal to 0.05 or 0.01) as one-dimensional variant analysis using SigmaPlot software version 12.0 (Systat Software Inc., San Jose, Calif., USA) for the data obtained from three independent experiments.

Example 1—in Silico Alanine Scanning Mutagenesis

For the analysis of the major residues required to construct a pharmacophore model, the alanine scanning mutagenesis technique was used. In the TLR2-TLR1-$Pam_3CSK_4$ complex, the residues of the binding site of $Pam_3CSK_4$ and TLR2-TLR1 were mutated to alanine, and the mutation energy was calculated based on the difference of the mutation and the wild-type binding free energy. The calculation was performed by using Calculate Mutation Energy (Binding) in Accelrys Discovery Studio (DS) 4.0 and residues with mutation energies greater than 0.5 kcal/mol are believed to affect binding of the receptor-ligand complexes because they make the binding unstable. The major residues affecting binding are illustrated in FIG. 2.

The values of the top ten unstable residues are illustrated in Table 2, and the values of all other residues are illustrated in Table 3.

TABLE 2

| Mutation to alanine | Mutation energy (kcal/mol) | Van der Waals term | Electrostatic term | Entropy term | Non-polar term |
|---|---|---|---|---|---|
| Phe349 | 4.55 | 8.1 | 0.17 | 0.52 | 0 |
| Tyr376 | 3.77 | 8.04 | −0.71 | 0.13 | 0 |
| Phe322 | 3.35 | 5.31 | −0.1 | 0.93 | 0 |
| Phe325 | 2.62 | 4.09 | 0.47 | 0.42 | 0 |
| Leu328 | 2.05 | 3.83 | −0.14 | 0.26 | 0 |
| Gln316* | 2.05 | 3.53 | 0.51 | 0.04 | 0 |
| Arg337* | 1.93 | 6.44 | 0.59 | −1.98 | 0 |
| Tyr326 | 1.8 | 4.63 | −0.12 | −0.57 | 0 |
| Leu312 | 1.79 | 2.96 | −0.07 | 0.43 | 0 |
| Leu350 | 1.73 | 2.86 | 0.28 | 0.2 | 0 |

*Residues of TLR1

TABLE 3

| Mutation to alanine | Mutation energy (kcal/mol) | van der Waals term | Electrostatic term | Entropy term | Non-polar term |
|---|---|---|---|---|---|
| Leu324 | 1.53 | 3.68 | −0.11 | −0.32 | 0 |
| Lys347 | 1.27 | 4.41 | −0.62 | −0.78 | 0 |
| Ile314 | 1.23 | 1.83 | −0.29 | 0.57 | 0 |
| Phe284 | 1.21 | 1.15 | 0.28 | 0.62 | 0 |
| Leu266 | 1.17 | 1.64 | −0.06 | 0.48 | 0 |
| Tyr320* | 1.17 | 1.26 | 0.44 | 0.4 | 0 |
| Ile341 | 1.15 | 1.84 | −0.08 | 0.34 | 0 |
| Leu355 | 1.15 | 1.65 | −0.03 | 0.42 | 0 |
| Asp327 | 1.13 | 2.54 | 0.14 | −0.26 | 0 |
| Val339* | 1.13 | 2.18 | −0.1 | 0.11 | 0 |
| Phe295 | 1.05 | 1.49 | 0.06 | 0.34 | 0 |
| Val343 | 1.02 | 1.84 | 0.08 | 0.08 | 0 |
| Pro352 | 0.98 | 1.48 | 0.3 | 0.11 | 0 |
| Leu334 | 0.96 | 1.54 | 0.02 | 0.23 | 0 |
| Val351 | 0.83 | 1.37 | 0.1 | 0.12 | 0 |
| Ile319 | 0.81 | 1.28 | 0.19 | 0.09 | 0 |
| Leu317 | 0.79 | 1.01 | 0.11 | 0.29 | 0 |
| Leu282 | 0.75 | 1.18 | 0.2 | 0.07 | 0 |
| Val311* | 0.72 | 2.21 | −0.06 | −0.44 | 0 |
| Val348 | 0.7 | 1.23 | 0.13 | 0.02 | 0 |
| Phe312* | 0.63 | 0.47 | −0.04 | 0.52 | 0 |
| Val309 | 0.56 | 0.91 | 0.01 | 0.13 | 0 |
| Val338 | 0.49 | 0.93 | −0.02 | 0.04 | 0 |
| Asn294 | 0.37 | 1.07 | 0.22 | −0.34 | 0 |
| Trp258* | 0.36 | 0.13 | 0.15 | 0.27 | 0 |
| Met270 | 0.33 | 0.61 | −0.18 | 0.14 | 0 |
| Leu289 | 0.31 | 0.6 | −0.13 | 0.09 | 0 |
| Pro315* | 0.28 | 0.5 | 0.09 | −0.02 | 0 |
| Phe323* | 0.24 | 0.03 | −0.01 | 0.29 | 0 |
| Ile319* | 0.16 | 0.06 | 0.07 | 0.12 | 0 |
| Phe314* | 0.14 | 0.1 | 0.17 | 0.01 | 0 |
| Tyr318* | 0.13 | 0.2 | −0.11 | 0.1 | 0 |
| Ile304* | 0.1 | 0.01 | 0.03 | 0.1 | 0 |
| Phe261* | 0.08 | 0.01 | −0.04 | 0.12 | 0 |
| Ile322* | 0.01 | 0.02 | 0.01 | 0 | 0 |
| Val333* | 0.01 | 0.02 | −0.04 | 0.02 | 0 |
| Leu265* | 0.01 | 0 | 0.01 | 0 | 0 |
| Ser346 | 0.01 | −0.07 | 0.09 | 0 | 0 |
| Val307* | −0.04 | 0.01 | −0.21 | 0.07 | 0 |
| Leu283* | −0.07 | −0.01 | −0.17 | 0.02 | 0 |
| Gly313* | −0.07 | −0.27 | −0.06 | 0.12 | 0 |
| Met338* | −0.13 | 0.08 | −0.38 | 0.03 | 0 |
| Thr336* | −0.27 | 0.08 | −0.64 | 0.01 | 0 |

*Residues of TLR1

The residues, which were calculated in Table 2 above and determined to affect binding capacity, were Phe325 and Phe349 of TLR2 and Gln316 of TLR1, confirming that they were identical to the major residues found in previous studies in biological experiments.

Accordingly, the three residues were found to play an important role in the process of forming protein-ligand complexes and were used to construct the following receptor-ligand-based pharmacophore models.

Example 2—Construction of a Receptor-Ligand-Based Pharmacophore Model

Figure 3:
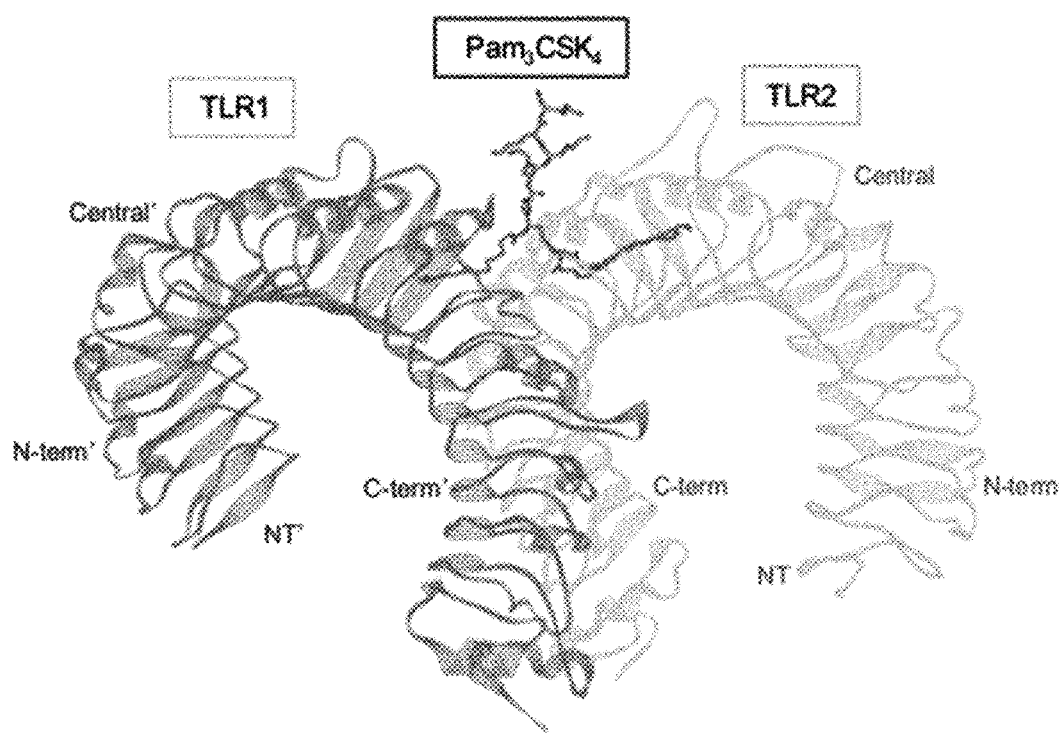
FIG. 3 is a diagram illustrating the crystal structure of a TLR2-TLR1-Pam$_3$CSK$_4$ complex used to construct a receptor-ligand-based pharmacophore model.

In order to construct a receptor-ligand-based pharmacophore model, the TLR2-TLR1-Pam$_3$CSK$_4$ complex was used to identify the characteristic of a ligand that allows binding with the receptor. The crystal structure of the complex is illustrated in FIG. 3.

Figure 4:
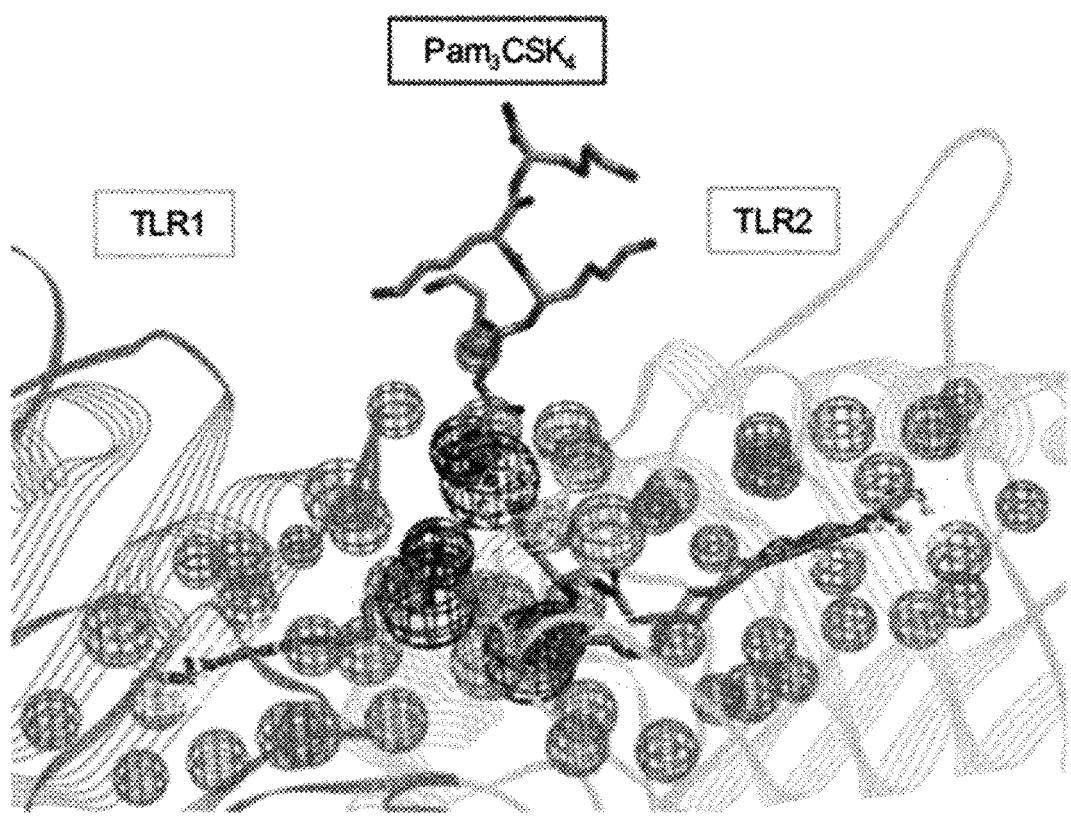
FIG. 4 is a diagram illustrating all pharmacophore characteristics obtained from Pam$_3$CSK$_4$ bound to TLR2-TLR1.

The Receptor-ligand Pharmacophore Generation protocol was used to target the lipopeptide binding site of the TLR2-TLR1-Pam$_3$CSK$_4$ complex together with the default parameters. As a result, all the characteristics of the pharmacophore based on the interaction of the TLR2-TLR1-Pam$_3$CSK$_4$ complex were confirmed and are illustrated in FIG. 4.

Figure 5:
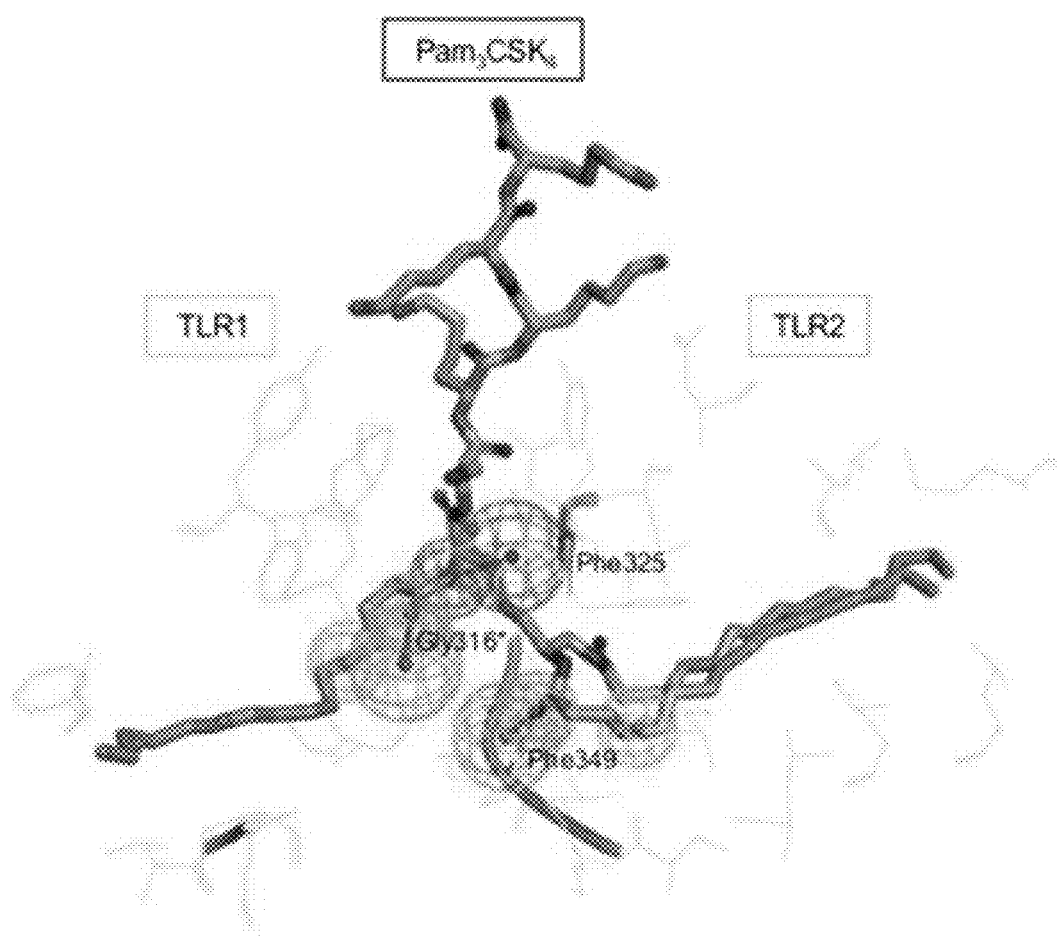
FIG. 5 is a diagram illustrating the characteristics of five selected pharmacophore characteristics in a receptor-ligand-based pharmacophore model and the surrounding of residues labeling the characteristics (asterisks: TLR1 residue, green spheres: HBA, purple spheres: HBD, blue spheres: HBY, gray spheres: space occupied by proteins).

All the above characteristics are selected with five characteristics and are illustrated in FIG. 5. The major characteristics were confirmed to be present in the active site around the major residues identified in Example 1 (Phe325 and Phe349 of TLR2 and Gln316 of TLR1), and the results are illustrated in FIG. 6.

Figure 6:
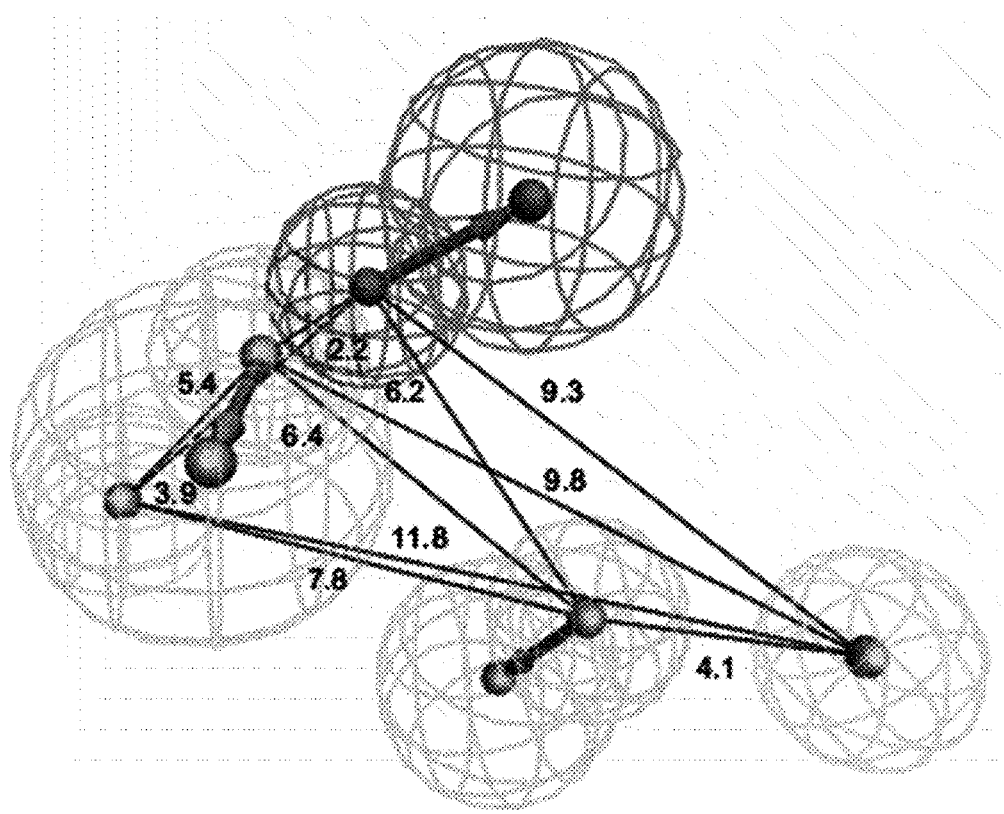
FIG. 6 is a diagram illustrating the major characteristics of a receptor-ligand-based pharmacophore model.

As illustrated in FIG. 5 and FIG. 6, it was confirmed that the ligand capable of binding with the protein had two hydrogen bond acceptors (HBA), one hydrogen bond doner (HBD), and two hydrophobic features (HBY).

Figure 7:
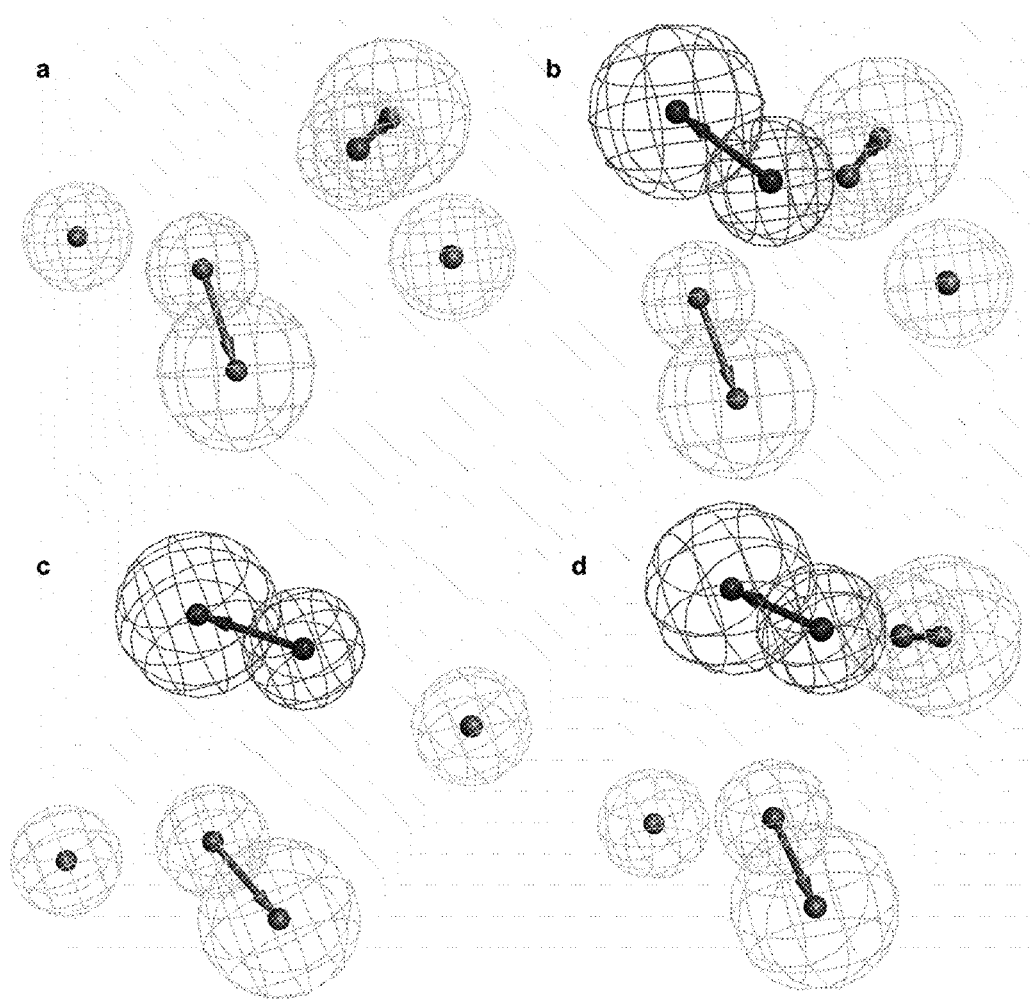
FIG. 7 is a diagram illustrating the results of constructing five characteristics selected from a receptor-ligand-based pharmacophore model into four sub-models.

The five characteristics identified above are again classified into four sub-models, as illustrated in FIG. 7.

Example 3—Construction of Ligand-Based Pharmacophore Model

Figure 8:
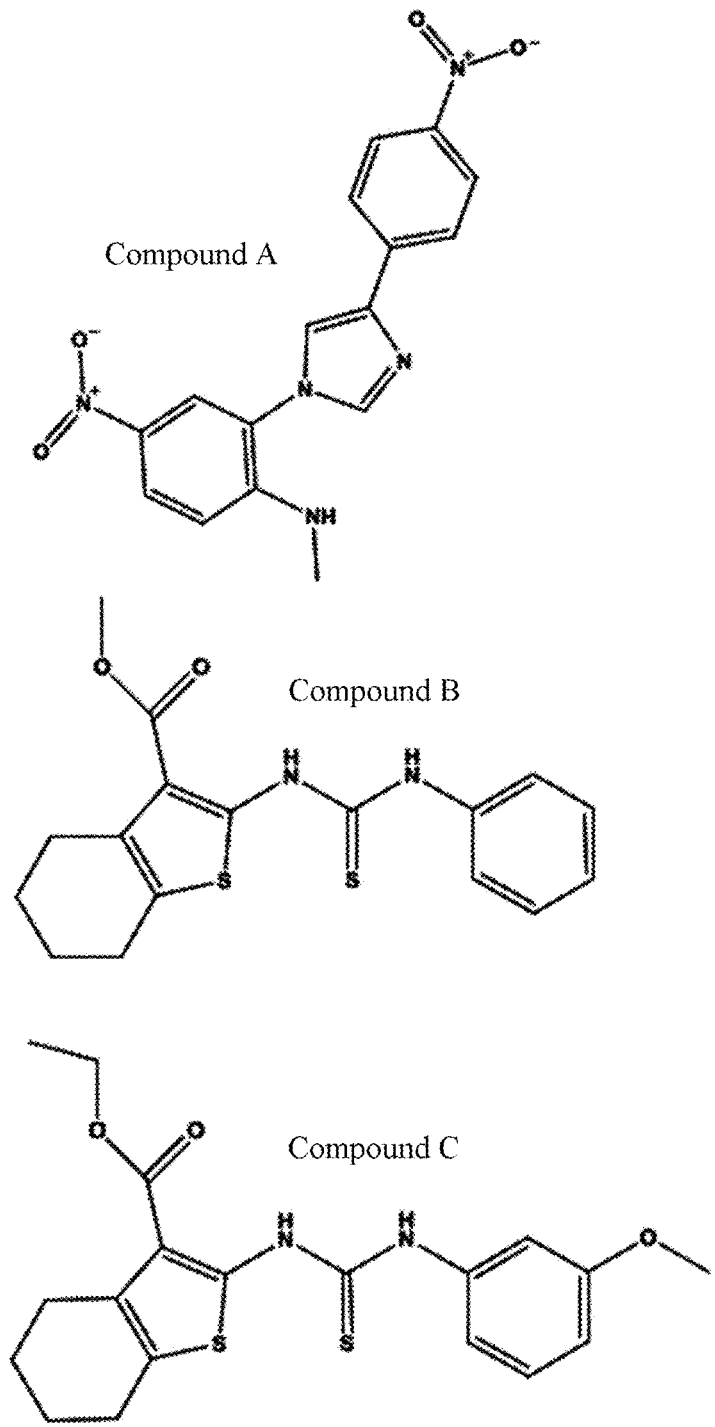
FIG. 8 is a diagram illustrating the structures of compounds A, B, and C used to construct a receptor-ligand-based pharmacophore model.

In order to construct a ligand-based pharmacophore model, compounds A, B, and C, which were known antagonists of small molecule TLR2, were used and their structures are illustrated in FIG. 8. Their two-dimensional structures were drawn using ChemBioDraw Ultra (CambridgeSoft). The characteristics of HBD, HBA, and HBY confirmed in Example 2 were also examined using the Common Feature Pharmacophore Generation protocol.

Figure 9:
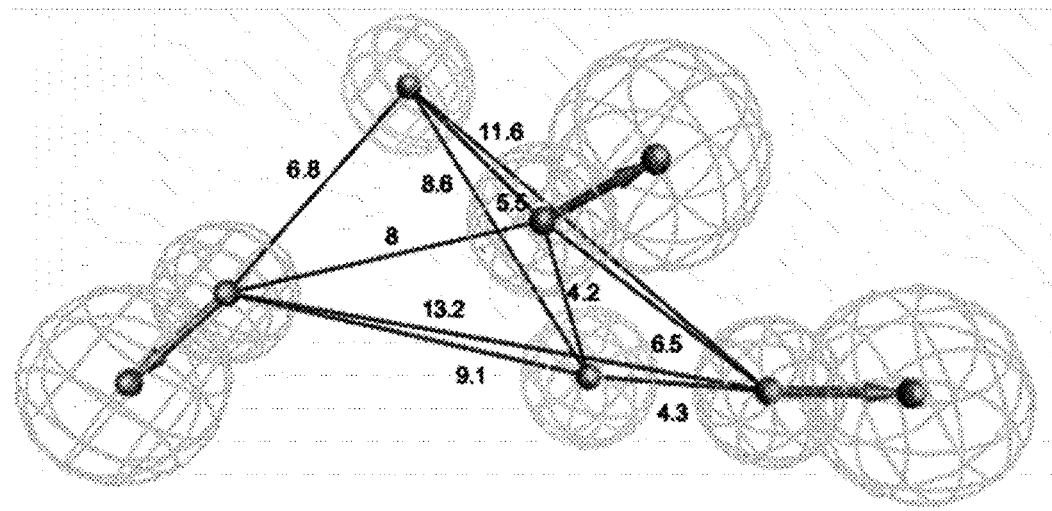
FIG. 9 is a diagram illustrating active molecules mapped from a ligand-based pharmacophore model 1 constructed from compound A.

Compound A was used as a query molecule in constructing the ligand-based pharmacophore model 1. From the various characteristics of Compound A, ten pharmacophore models were constructed, of which three HBAs and two HBYs were constructed as ligand-based pharmacophore model 1. Based thereon, an active molecule was mapped and the result is illustrated in FIG. 9.

Compound B was used as a query molecule in constructing a ligand-based pharmacophore model 2. The characteristics of the pharmacophore confirmed from Compound B were confirmed to be one HBD, two HBAs, and two HBYs, and mapping results based thereon are illustrated in FIG. 10.

Figure 10:
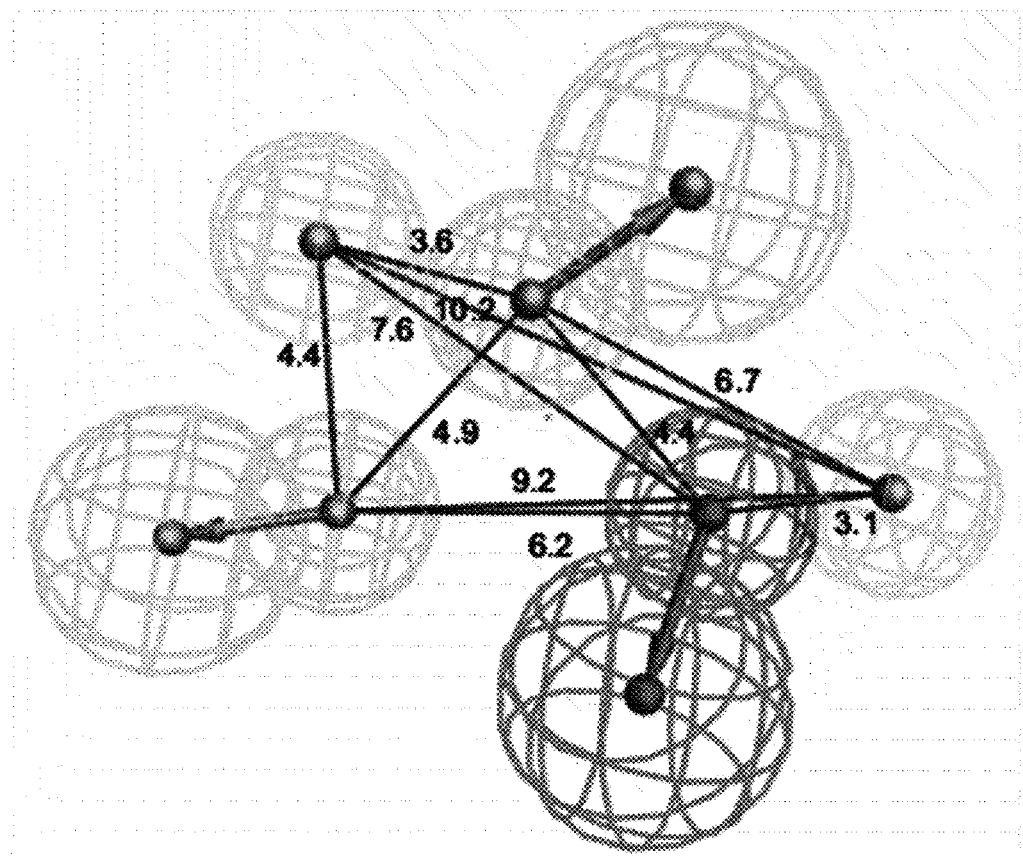
FIG. 10 is a diagram illustrating active molecules mapped from a ligand-based pharmacophore model 2 constructed from compounds B and C.

In addition, it was confirmed that the result of mapping the characteristics confirmed from Compound C is the same as in FIG. 10 because of the structural similarity between the Compound C and Compound B.

Example 4—Screening Using a Fit Value

Four sub-receptor-ligand-based pharmacophore models constructed in Example 2 above were used to screen TLR2 antagonist candidate materials from a commercially available library of approximately 7 million molecules. The Search 3D Database of DS 4.0 was used and each of the above four models was set as an input. The Best Search method was used to calculate the fit value of the ligand to the pharmacophore model. Based on this value, 500 molecules (hits) that were ideally mapped to each model were obtained. As a result, 2000 hit molecules were selected from a total of four models.

Example 5—Screening Using Molecular Similarity

In order to select TLR2 antagonist candidate materials from a commercially available library of about 7 million molecules, in accordance with the same method as in Example 4 above, 2,312,604 hit molecules were selected from the ligand-based pharmacophore model 1 with Compound A as an input and 1,651,005 hit molecules were selected from the ligand-based pharmacophore model 2 with Compound B as an input.

In order to further select the 3,963,609 hit molecules selected from the two models, the scoring function of ROCS_tanimoto-Combo according to the shape and atomic type similarity of the query and hit molecules was used. Compound A was used as a query molecule for comparison with 2,312,604 hit molecules obtained from the ligand-based pharmacophore model 1, and Compounds B and C were used as a query molecule for comparison with 1,651,005 hit molecules obtained from the ligand-based pharmacophore model 2. As a result of the scoring, a total of 1,500 hit molecules were selected from the ligand-based pharmacophore model.

Example 6—Screening of Drug-Like Compounds

In order to further screen drug-like compounds required for the development of new drugs among the 2,000 hit molecules obtained in Example 4 above and 1,500 hit molecules obtained in Example 5 above, that is, a total of 3,500 hit molecules, Lipinski and Veber rule and ADMET (absorption, distribution, metabolism, excretion, toxicity) characteristics were used.

Specifically, the Lipinski and Veber rules were used as a filter for screening compounds with better oral bioavailability. The characteristics of ADMET (absorption, distribution, metabolism, excretion, toxicity) were used to identify good absorption, adequate solubility, low blood-brain penetrability, cytochrome P450 2D6 non-inhibition, non-hepatocellular toxicity, and non-plasma protein binding ability.

As a result, 1,126 molecules selected as drug-like compounds from a total of 3,500 hit molecules were confirmed. The drug-like characteristics of the candidate compounds were calculated and selected to exclude molecules that were not available at the drug development stage.

Example 7—Molecular Docking and Scoring

The molecular docking of the TLR2-TLR1 dimer was used to select the optimal docking pose and screen ligand for ligand-receptor binding. The ligand was prepared with the Prepare Ligand module of DS 4.0. The binding site of the lipopeptide was selected as the docking site. For optimal screening, the screening was performed using two programs: CDocker (using CD, CHARMM force field) and AutoDock (AD) Vina.

Figure 11:
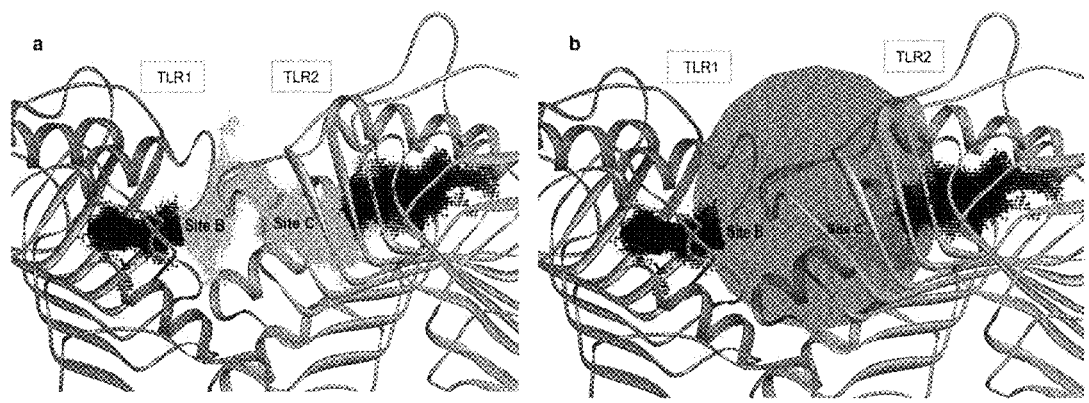
FIG. 11 is a diagram illustrating molecular docking using CDocker.
Figure 13A:
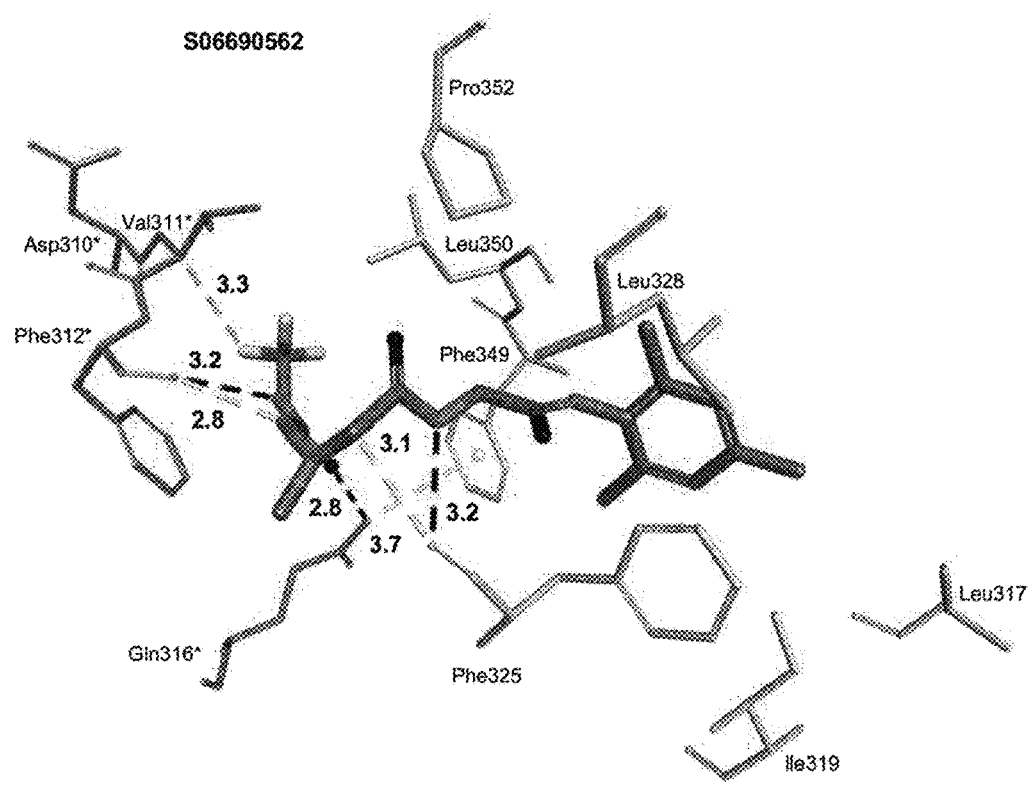
FIG. 13A is a diagram illustrating the results of the docking of the screened compound S06690562.
Figure 13B:
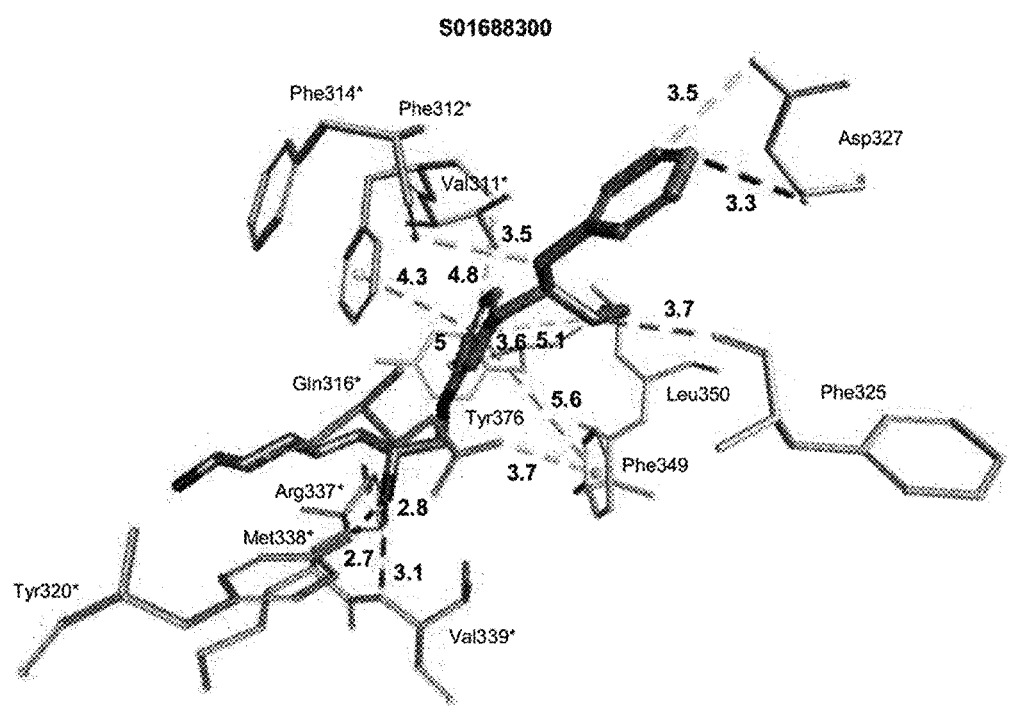
FIG. 13B is a diagram illustrating the results of the docking of the screened compound S01688300.
Figure 13C:
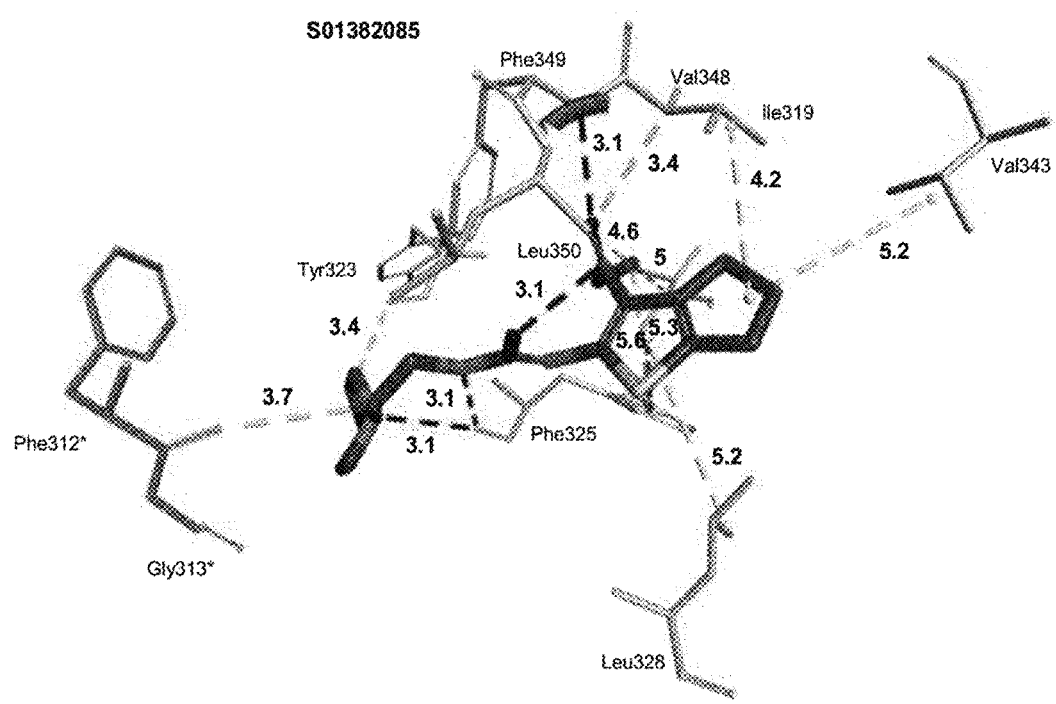
FIG. 13C is a diagram illustrating the results of the docking of the screened compound S01382085.
Figure 14A:
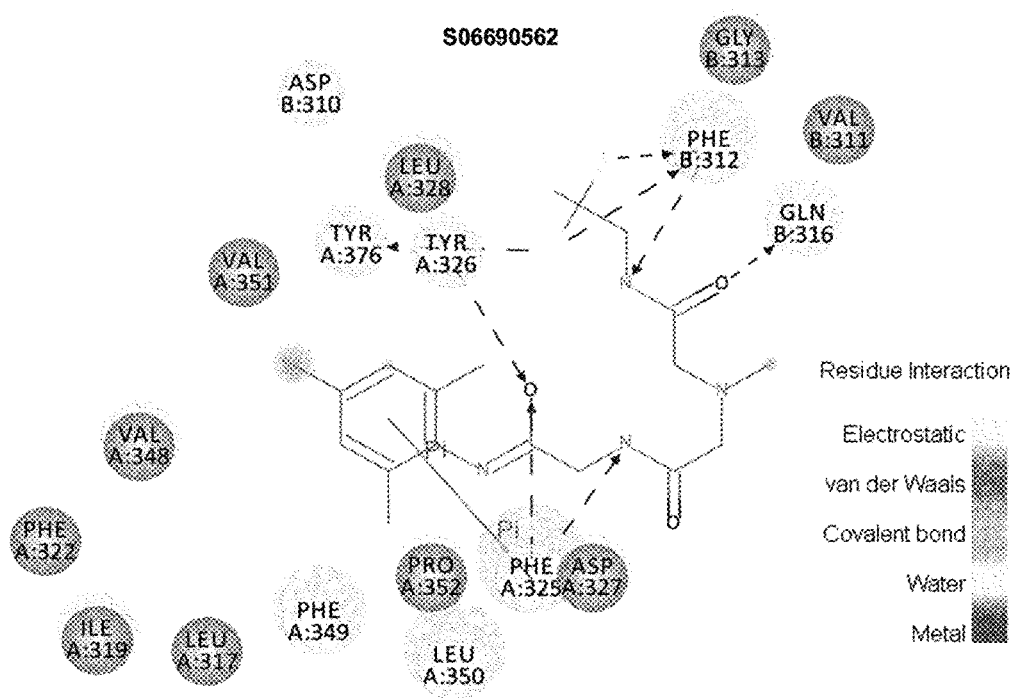
FIG. 14A is a diagram illustrating the results of the docking of the screened compound S06690562.
Figure 14B:
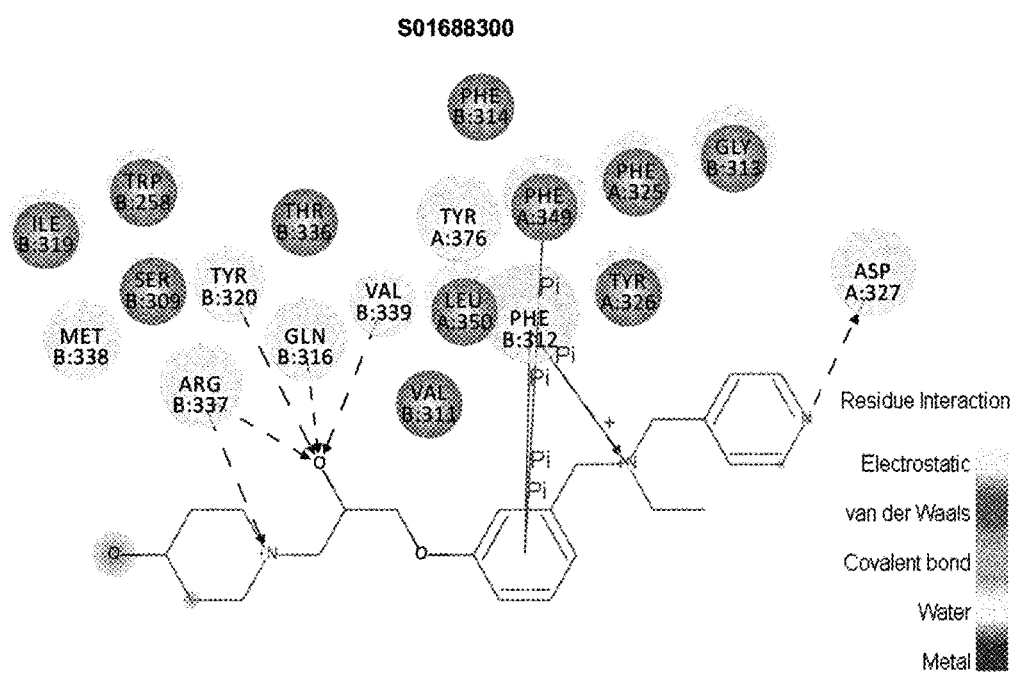
FIG. 14B is a diagram illustrating the results of the docking of the screened compound S01688300.
Figure 14C:
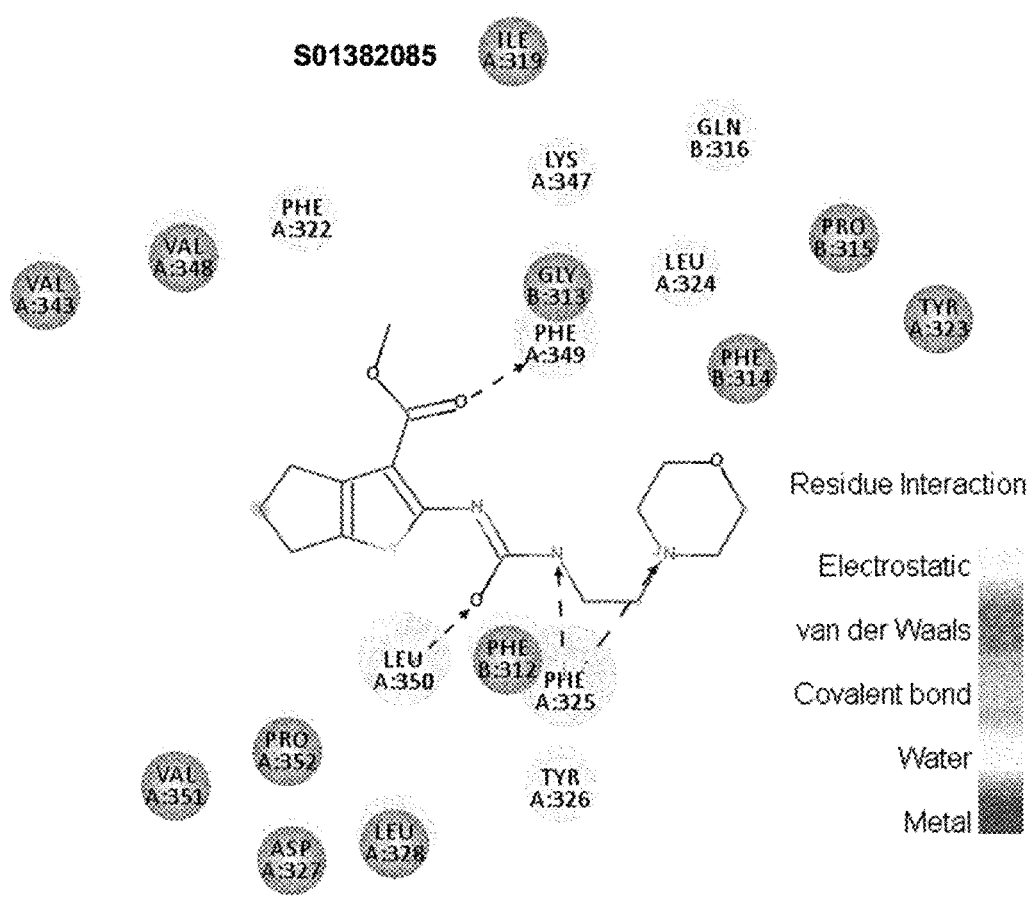
FIG. 14C is a diagram illustrating the results of the docking of the screened compound S01382085.

More specifically, the 1,126 drug-like compounds obtained in Example 6 above were docked to four $Pam_3CSK_4$ sites using CD. At this time, as illustrated in FIG. 11, spheres having a radius of 13 Å, which mostly cover the sites B and C, were used. The CD interaction energy was calculated, and as a result, the top 100 poses of about 60 compounds were screened.

The 100 poses were re-docked using AD Vina. At this time, the dock_runscreening protocol was applied. As a result, the top 26 poses with excellent docking were screened based on the AD affinity energy value.

Example 8—Rescoring of Docking Complexes

Docking complex scoring was performed using binding free energy to determine the driving force of protein-ligand interaction.

Specifically, to quantify the thermodynamic interactions of the TRL2-TLR1 complex with the ligand, the 26 docking complexes obtained in Example 7 above were aligned again in accordance with the molecular dynamics (MD) according to the calculation of Poisson-Boltzmann surface area (MM/PBSA) binding free energy. The MD simulation was performed using the g_mmpbsa tool, and the average binding energy and its standard deviation/error were calculated as MnPbSaSatat.pyscript.

The MM/PBSA binding free energy was calculated by the following Equation 1.

$$\Delta G_{bind} = \Delta G_{complex} - (\Delta G_{protein} + \Delta G_{ligand})$$ [Equation 1]

$G_{bind}$ is the average binding free energy, $G_{complex}$ is the binding free energy of the TRL2-TLR1 complex, $G_{protein}$ is the binding free energy of the protein (receptor), and $G_{ligand}$ is the binding free energy of the ligand.

Three compounds (S06690562, S01688300, S01382085) were selected based on the average MM/PBSA value obtained by the above calculation, the AD binding energy value of Example 7 above, and the CD binding energy value. As a result, two compounds from the receptor-ligand-based model and one compound selected from the ligand-based model were confirmed and their two-dimensional structure is illustrated in FIG. 12. The molecular docking results thereof are illustrated in FIGS. 13A to 13C and FIGS. 14A to 14C.

Example 9—Confirmation of IL-8 Secretion

Among the 26 compounds screened in Example 7 above, 19 compounds (S02546436, S02276077, S06696686, S06690562, S06713271, S02396152, 501525559, S06542401, S01739292, S01688300, S06570841, S06570001, S06568641, S06572801, S01577528, S01382085, S01442577, S01414289, S01292238) were treated to confirm whether they exhibit biological activity as an antagonist of TLR2, and the secretion change of IL-8, a cytokine induced by TLR2, was confirmed.

HEK293-TLR2 (expressed at endogenous levels of TLR1) and HEK293-Null cell lines were cultured in 96-well tissue culture plates (BD Biosciences) at a density of $1\times10^4$ cells/wells, 37° C., 95% air and 5% $CO_2$ for 24 hours. In order to determine the agonist activity, a cell stimulation was achieved by treatment with 50 μM of compound and 50 nM of $Pam_3CSK_4$ (Invivogen, San Diego, Calif., USA). In order to determine the antagonist activity, cells were treated with various concentrations of compound for 1 hour and then co-treated with 50 nM of $Pam_3CSK_4$. The next day, IL-8 secretion was quantified by human IL-8 ELISA Ready-SET-Go! ® (Second generation) kit (eBioscience, San Diego, Calif., USA) according to the method of the manufacturer's guide, and the quantified results are illustrated in FIG. 15.

Figure 15:
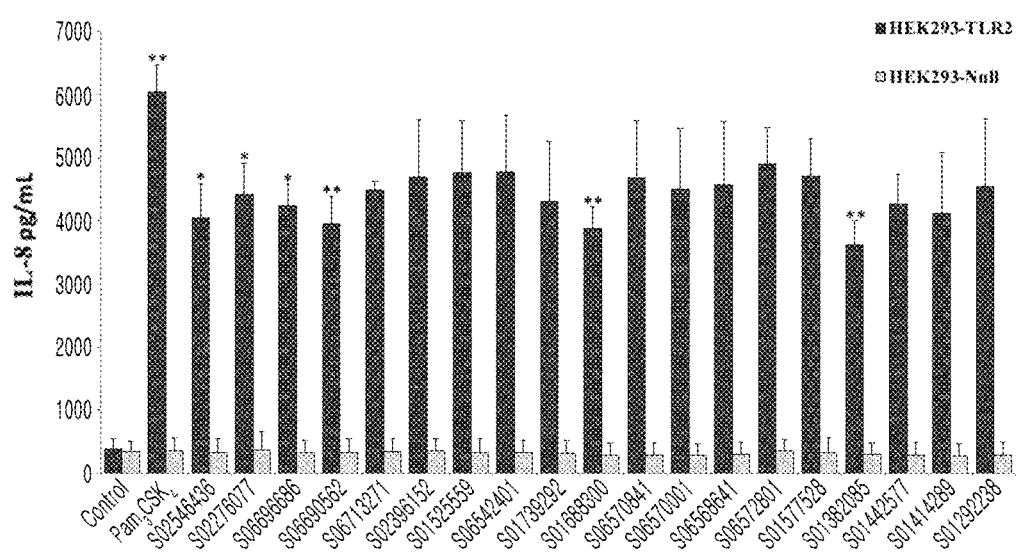
FIG. 15 is a diagram confirming the secretion of IL-8 by treating 19 compounds with cells (* $P<0.05$, ** $P<0.01$).

As illustrated in FIG. 15, it was confirmed that all 19 compounds reduced the secretion of IL-8, and in particular, $Pam_3CSK_4$-induced IL-8 secretion amount was greatly reduced when 6 compounds (S02546436, S02276077, S06696686, S06690562, S01688300, S01382085) were treated. Accordingly, it was confirmed that the above six compounds act as antagonists of TLR2 and significantly reduce the secretion of IL-8.

For the dose-dependent analysis of the top three compounds (S06690562, S01688300, S01382085) among the six compounds, the concentrations of the three compounds were varied to 12.5, 25, and 50 μM, and the secretion amount of IL-8 was analyzed as the above method. The results are illustrated in FIG. 16.

Figure 16:
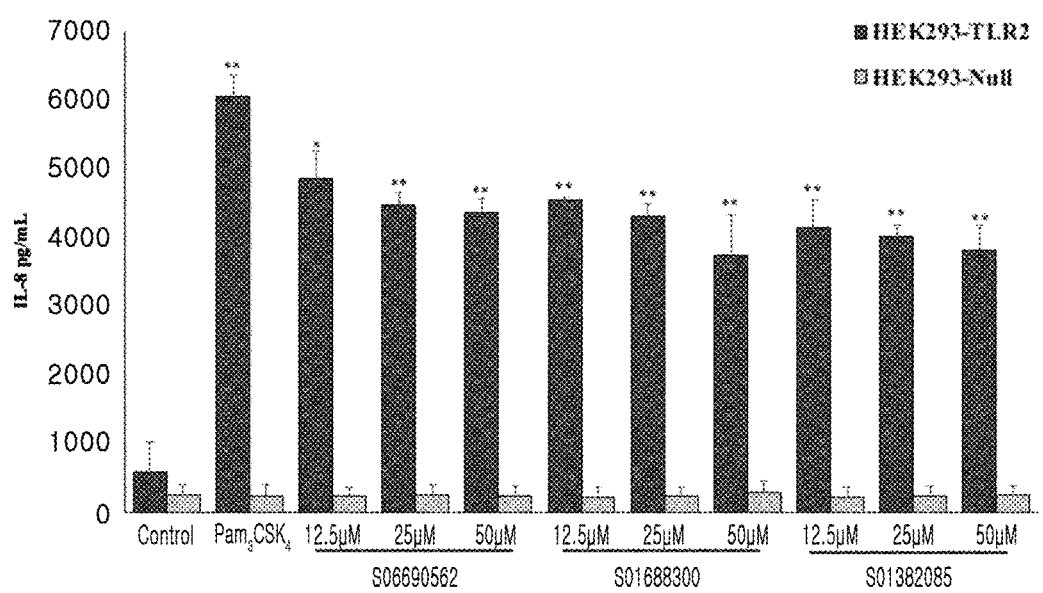
FIG. 16 is a diagram illustrating the results of inhibition of concentration-dependent IL-8 secretion of three screened compounds (S06690562, S01688300, S01382085) (*$P<0.05$, **$P<0.01$).

As illustrated in FIG. 16, the secretion of IL-8 was significantly reduced when the compound was treated at a high concentration of 50 μM as compared with the case where all three compounds were treated at a low concentration. Accordingly, it was confirmed that the three compounds are substances that decrease the secretion of IL-8 in a dose-dependent manner.

Example 10—Cell Culture and Cell Viability Analysis

HEK293-TLR2 and HEK293-Null cell lines (Invivogen, San Diego, Calif., USA) were cultured with 10% heat-inactivated FBS (fetal bovine serum, Thermo Fisher Scientific Inc.), 50 IU/mL penicillin, 50 µg/mL streptomycin (Thermo Fisher Scientific Inc.), and Dulbecco's modified Eagle's medium (Thermo Fisher Scientific Inc., MA., USA) supplemented with Normocin™ 100 mg/mL (Invivogen., San Diego, Calif., USA). The compounds were dissolved in dimethyl sulfoxide (Sigma-Aldrich, St. Louis, Mo., USA) in brown tubes and stored at a concentration of 10 mM.

In order to confirm the cytotoxicity of the three compounds screened in Example 8 above (S06690562, S01688300, S01382085), the MTS technique was performed in HEK293-TLR2, and the results are illustrated in FIG. 7.

Specifically, cell activity was measured using the CellTiter 96® AQueous One Solution Cell Proliferation Assay (MTS assay; Promega, Madison, Wis., USA) according to the manufacturer's guidelines. Cells were cultured in 96-well plates at a concentration of $5\times10^3$ cells/mL and maintained overnight at 37° C. in a humidified atmosphere containing 5% $CO_2$. The next day, the cultured cells were treated with three concentration conditions (12.5 µM, 25 µM, and 50 µM) of three screened compounds (S06690562, S01688300, S01382085). After 24 hours, the MTS solution was treated in wells and the absorbance was measured at 490 nm with a microplate spectrophotometer system (Molecular Devices Inc.). The results are illustrated in FIG. 17.

Figure 17:
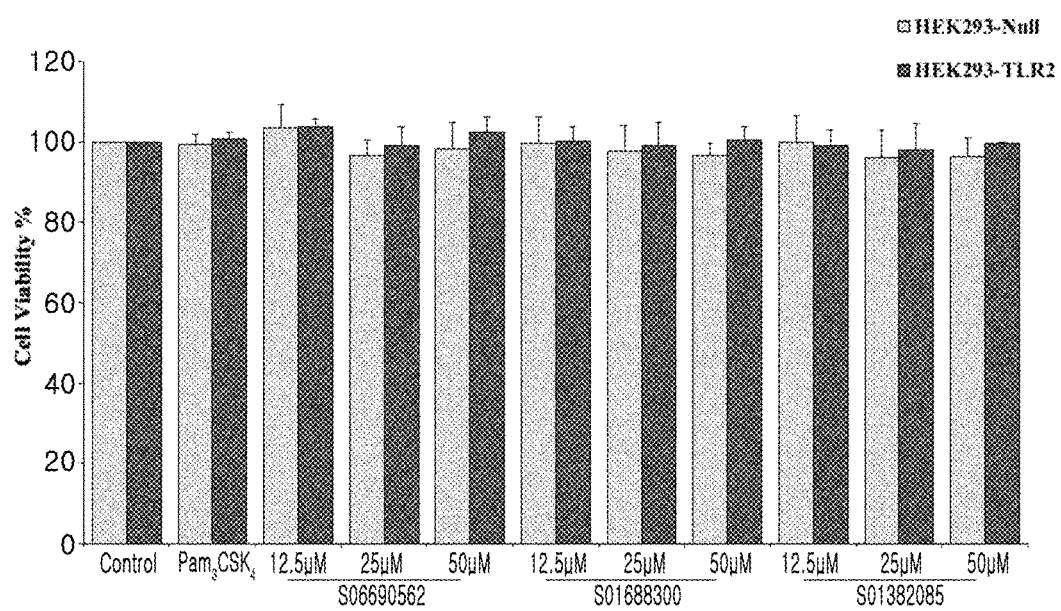
FIG. 17 is a diagram confirming the cytotoxicity of three screened compounds (S06690562, S01688300, S01382085).

As illustrated in FIG. 17, it was confirmed that all of the above three compounds showed no cytotoxicity at a concentration of 12.5 µM, 25 µM, and 50 µM, and thus they are safe materials and can be used as drugs.

INDUSTRIAL APPLICABILITY

The novel TLR2 antagonist according to the present disclosure effectively inhibits IL-8 secretion and does not cause toxicity in vivo, and thus can be usefully used in pharmaceutical compositions for the prevention or treatment of inflammatory diseases. Since the TLR2 antagonist has a small molecular weight and a high oral bioavailability, it can be effectively used as an oral administration agent and can also be used as a regulator of TLR4.

The invention claimed is:

1. A method of treating Crohn's disease comprising administering to a subject in need thereof a pharmaceutical composition comprising an effective amount of a TLR2 (Toll-like receptor 2) antagonist S01382085 represented by the following Formula 1:

[Formula 1]

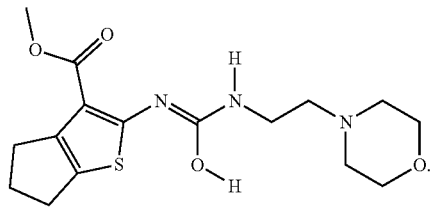

2. The method of claim 1, wherein the pharmaceutical composition is an oral formulation.

* * * * *